United States Patent [19]

Helmich

[11] Patent Number: 4,724,048
[45] Date of Patent: Feb. 9, 1988

[54] WATER DISTILLER

[76] Inventor: Arthur R. Helmich, Rte. 5, Box 5150, Benton, Ark. 72015

[21] Appl. No.: 772,613

[22] Filed: Sep. 4, 1985

Related U.S. Application Data

[63] Continuation-in-part of Ser. No. 508,046, Jul. 27, 1983, abandoned.

[51] Int. Cl.⁴ .............................................. B01D 3/02
[52] U.S. Cl. .................................. 202/176; 202/180; 202/195; 202/235; 202/242; 203/2; 203/4; 203/22; 203/39; 203/DIG. 8; 159/23; 159/44; 159/DIG. 32; 159/DIG. 41
[58] Field of Search ............ 202/176, 160, 195, 185.1, 202/242, 235, 254, 180, 160, 206, 237; 203/1, 2, 10, 12, 4, 39, DIG. 8, 22; 159/23, 44, DIG. 32, DIG. 41; 55/36

[56] References Cited

U.S. PATENT DOCUMENTS

| 771,832 | 10/1904 | Rochlitz | 202/196 |
|---|---|---|---|
| 1,076,410 | 10/1913 | Dunnam | 202/194 |
| 3,029,068 | 4/1962 | Skow | 202/177 |
| 3,312,600 | 4/1967 | Morton | 202/236 |
| 3,444,050 | 5/1969 | Sundquist | 203/10 |
| 3,445,344 | 5/1969 | Morton | 202/236 |
| 3,489,649 | 1/1970 | Weiss | 202/172 |
| 3,660,246 | 5/1972 | Smith | 203/10 |
| 3,838,016 | 9/1974 | Powers | 202/181 |
| 3,907,683 | 9/1975 | Gilmont | 203/10 |
| 4,045,193 | 8/1977 | Cooksley | 202/196 |
| 4,110,170 | 8/1978 | Kirschman et al. | 202/180 |
| 4,139,418 | 2/1979 | Sech | 202/181 |
| 4,239,601 | 12/1980 | Lemoine | 203/2 |
| 4,331,514 | 5/1982 | Bauer | 202/196 |
| 4,339,307 | 7/1982 | Ellis, Jr. | 203/10 |

FOREIGN PATENT DOCUMENTS 0029737 of 1909 United Kingdom ................ 202/177

*Primary Examiner*—S. Leon Bashore
*Assistant Examiner*—V. Manoharan
*Attorney, Agent, or Firm*—Hill, Van Santen, Steadman & Simpson

[57] ABSTRACT

A water distiller apparatus for purifying and degassing domestic water supplies is provided which is constructed for easy cleaning of all parts and in which inflowing water is preheated by condensing steam within a condenser which preheating allows dissolved gases to dissipate through a vent before the inlet water reaches an evaporator portion. The rate of inflowing water is controlled by a temperature responsive valve that is in thermal communication with the condenser to maximize heat transfer and minimize heat and water loss.

12 Claims, 13 Drawing Figures

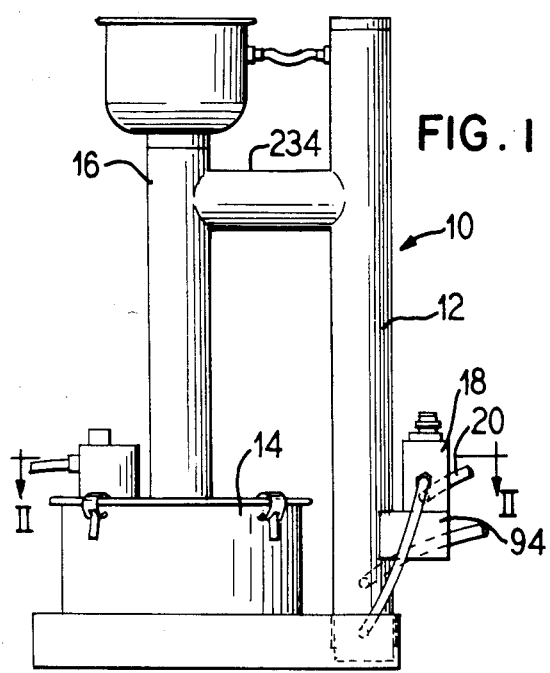
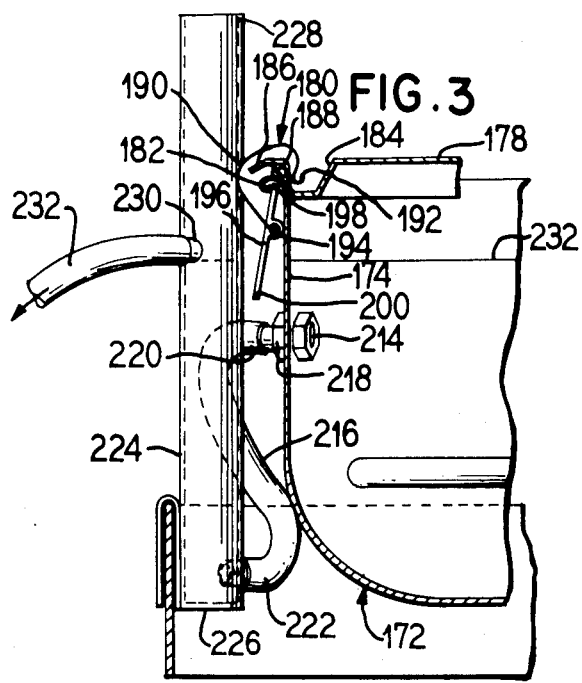
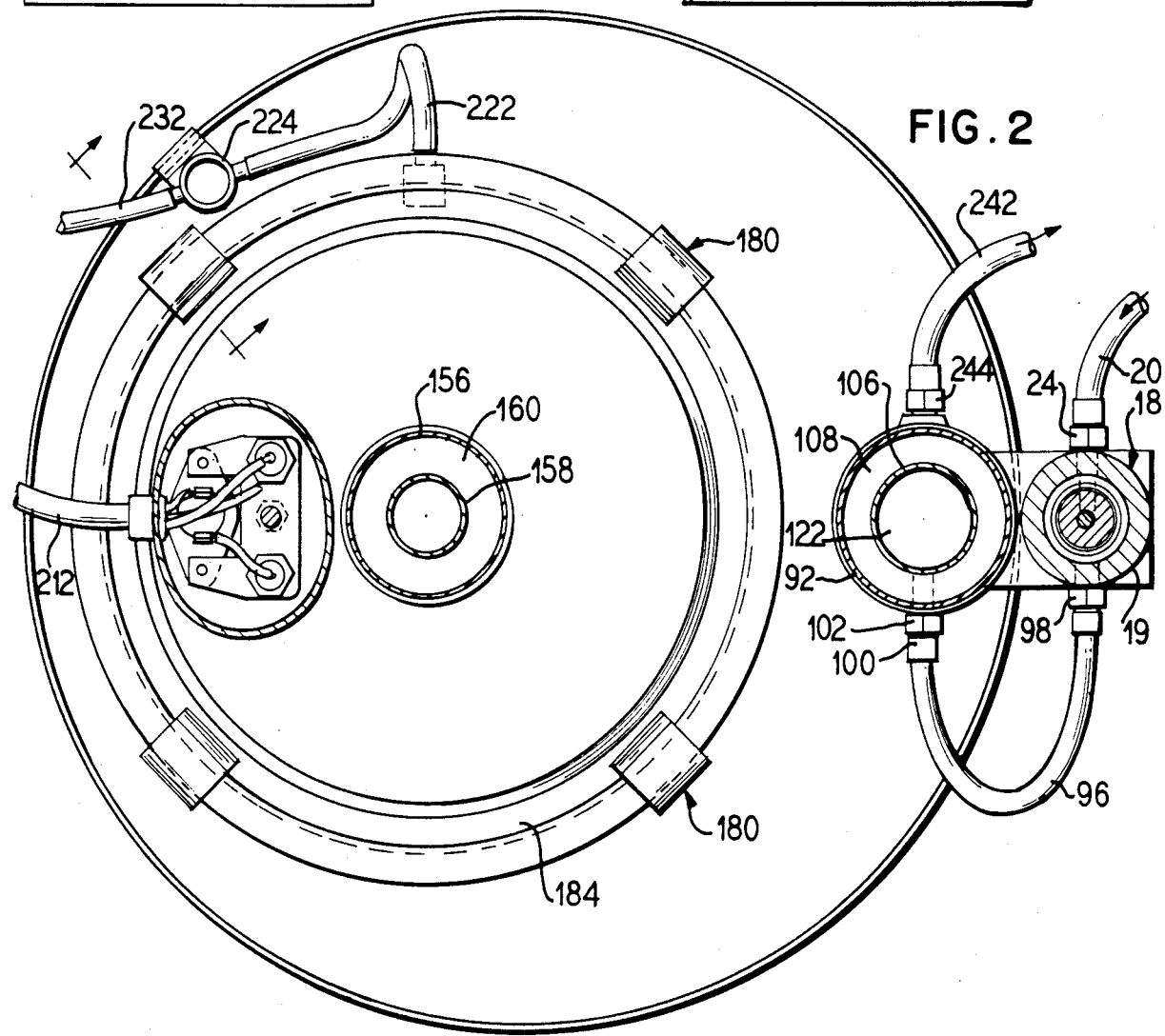

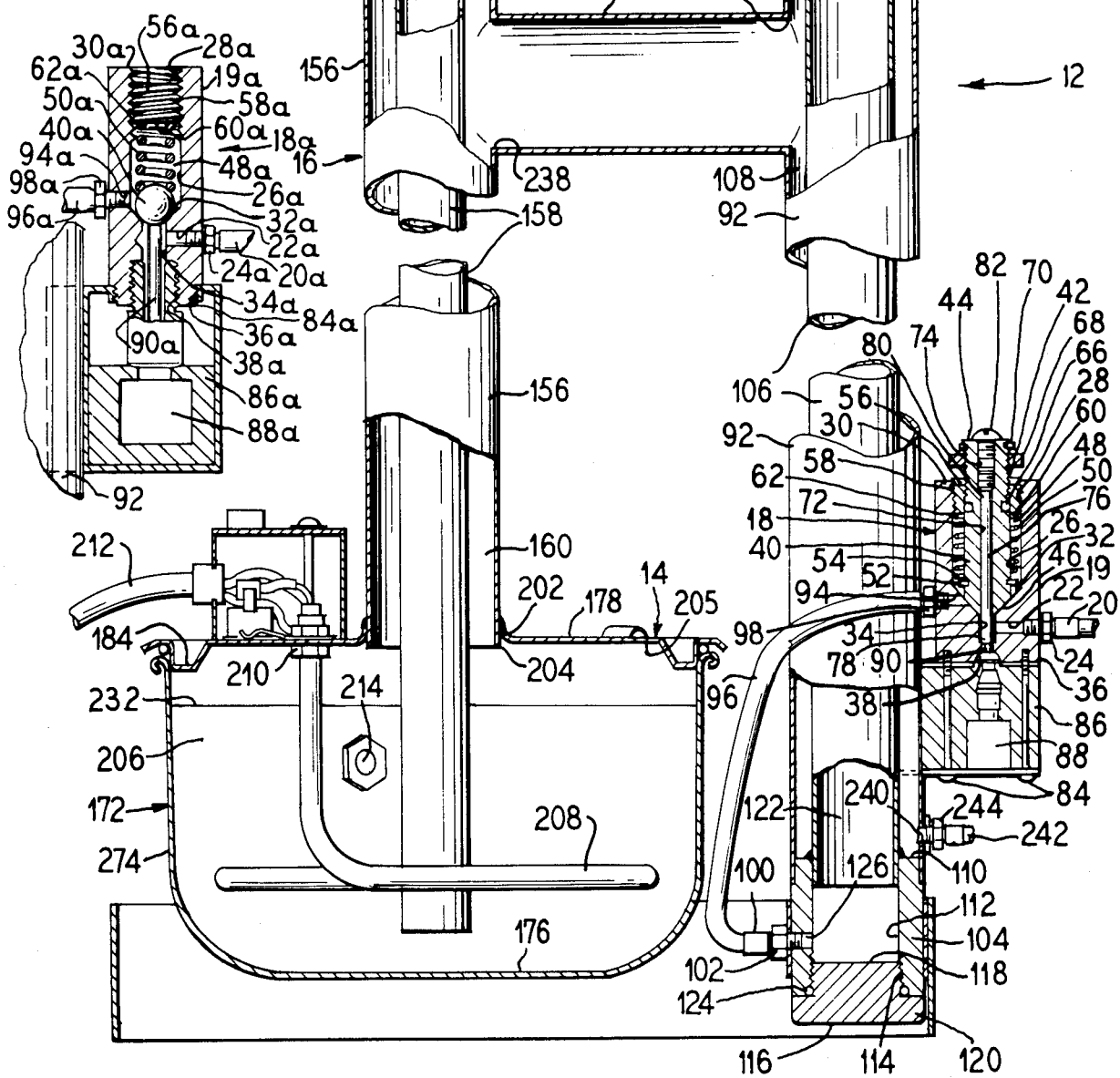

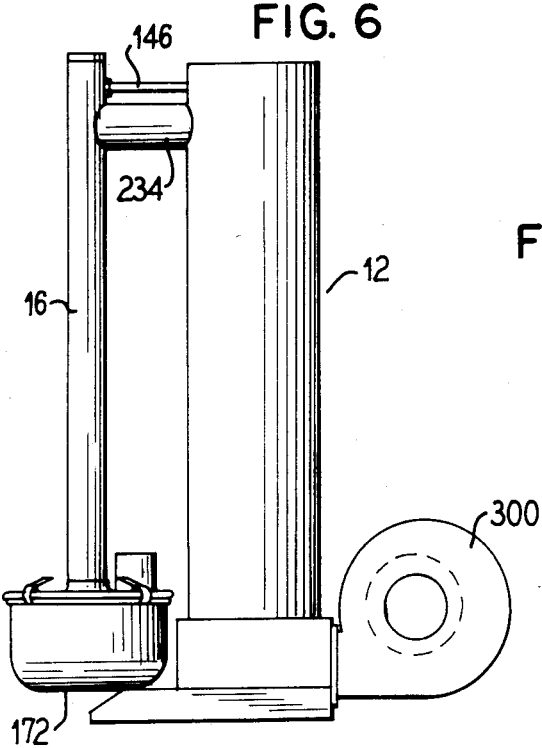
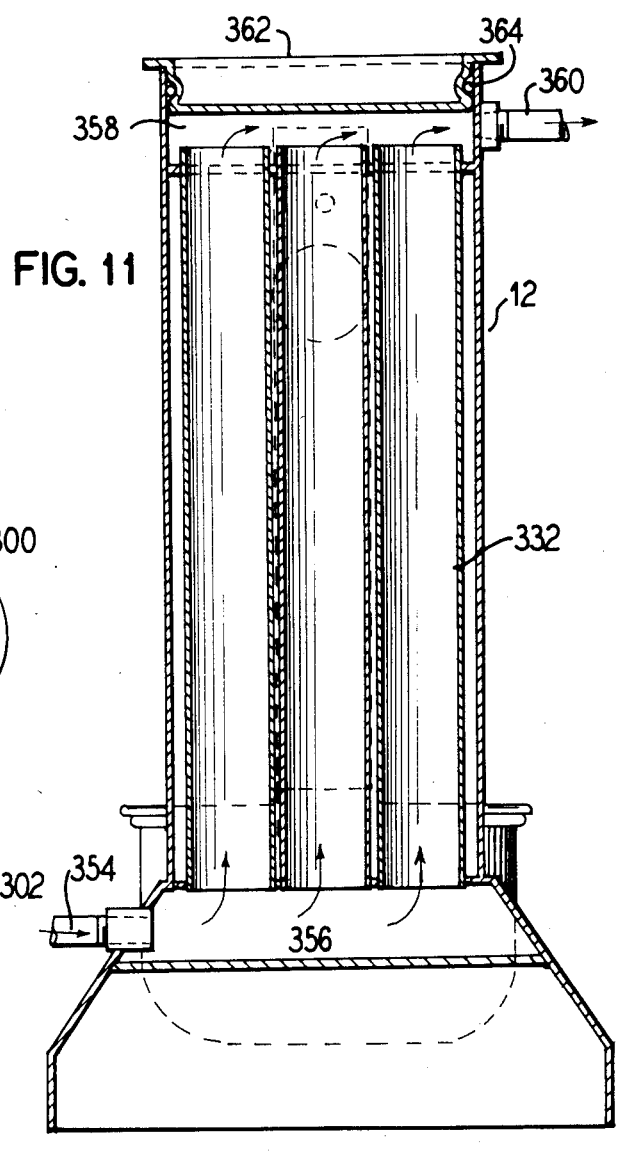
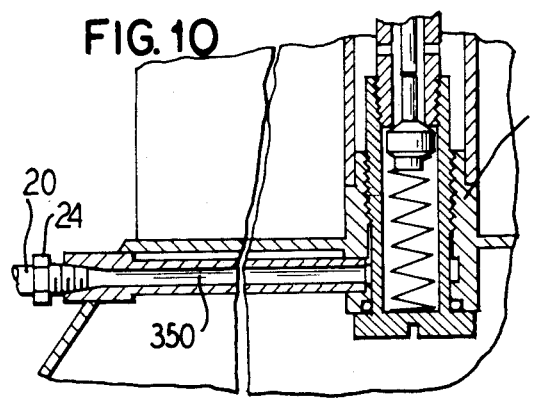
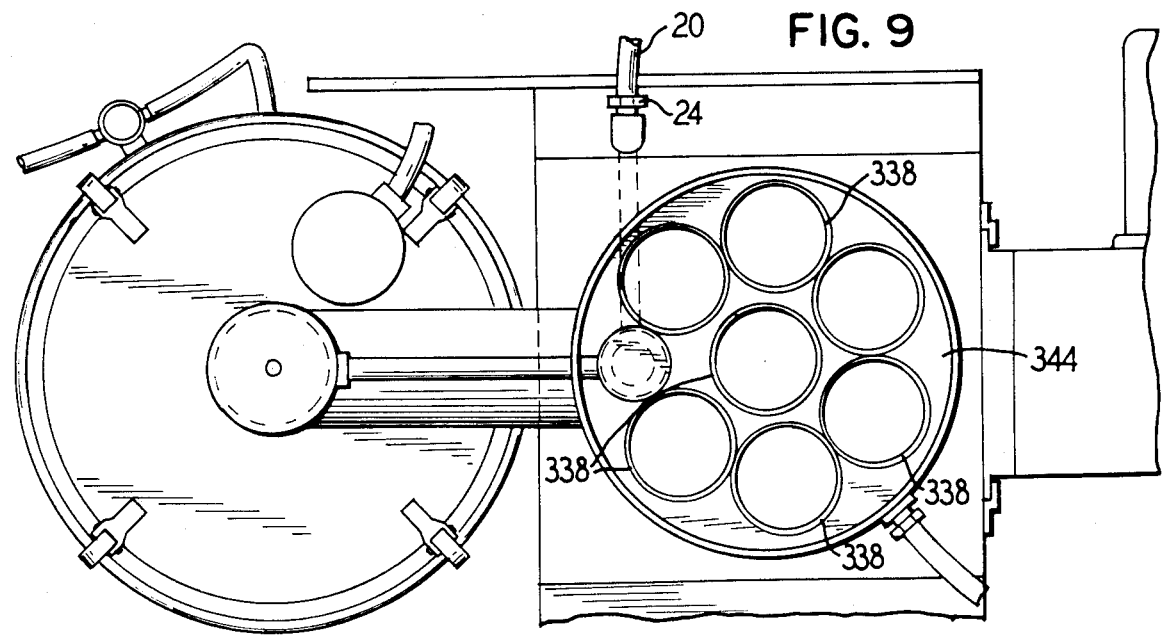

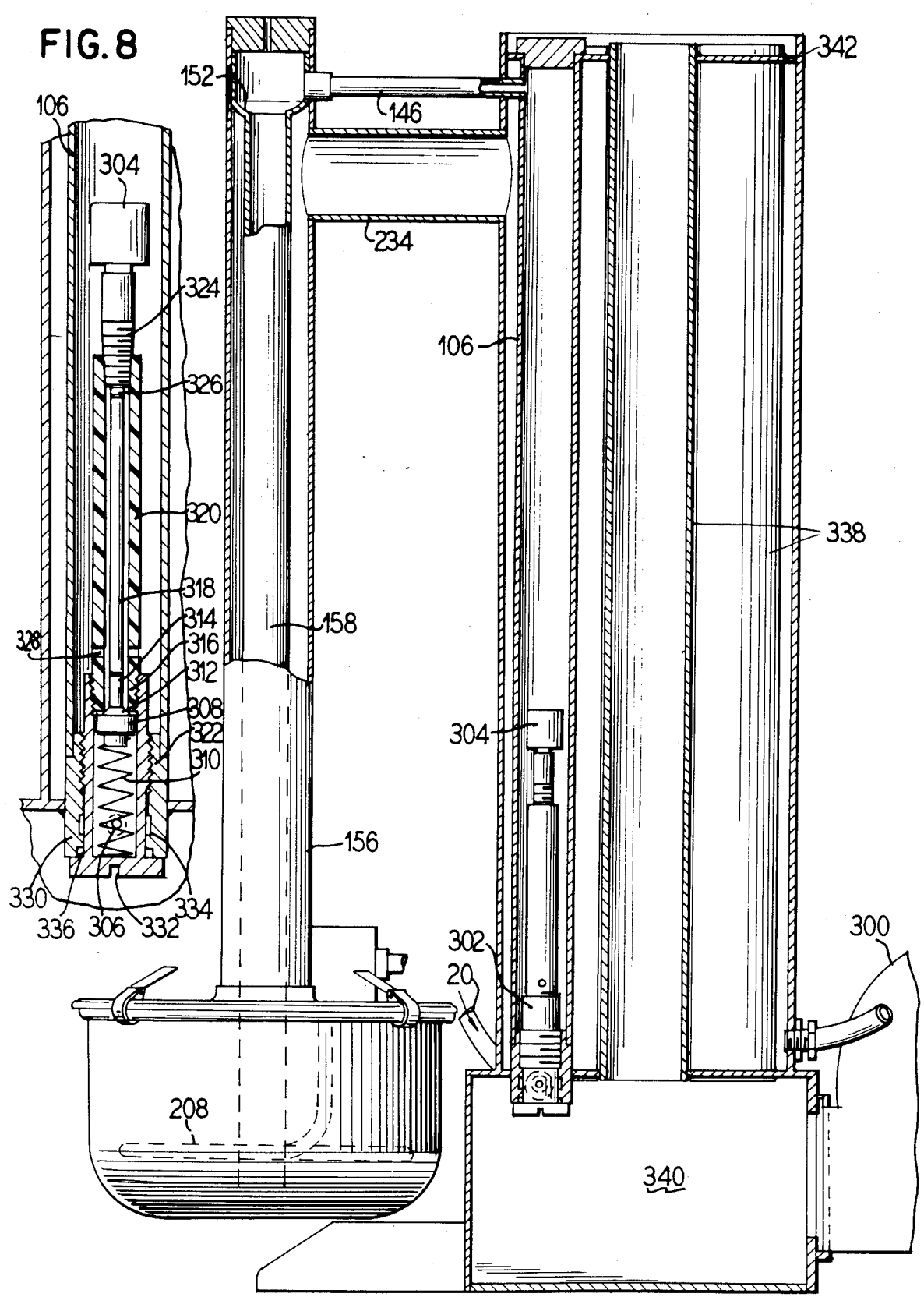

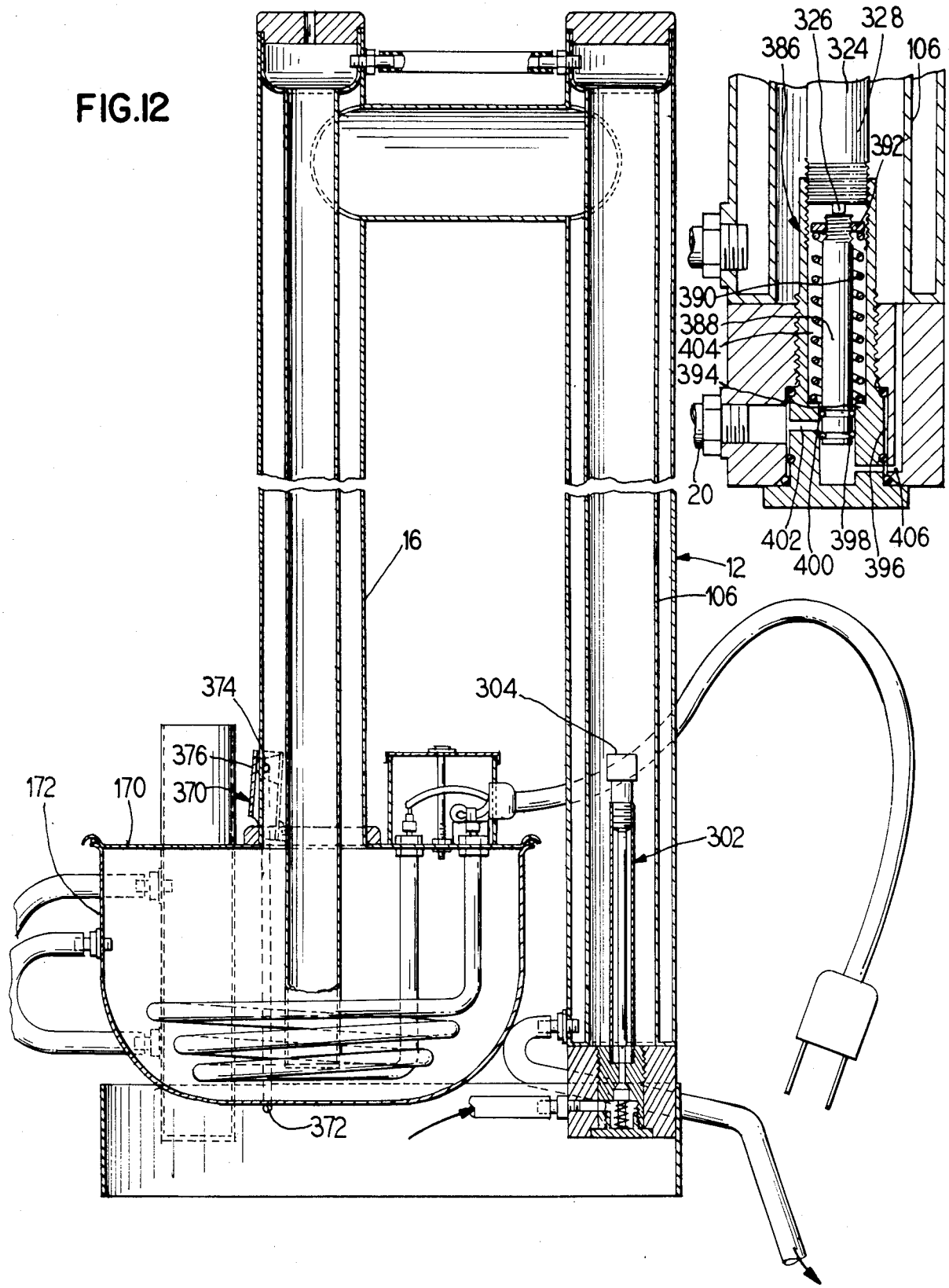

WATER DISTILLER

This application is a continuation-in-part of my copending patent application Ser. No. 508,046, filed June 27, 1983, and now abandoned, the teachings of which are incorporated herein by reference.

BACKGROUND OF THE INVENTION

1. Field of the Invention

The present invention relates to water distillers and, more particularly, to a domestic size water distiller which has means for venting dissolved gases and an automatic thermally controlled water supply valve.

2. Description of the Prior Art

Many types of water distilling apparatus are known for purifying water for in-home use. Many of the known water distillers control the inflow of water via a valve. A variety of means are disclosed for controlling the valve. Kirschman et al U.S. Pat. No. 4,110,170 discloses a home water distiller having a thermoresponsive valve 17 mounted on a water output 19 spaced from the device, which, through the action of an expansion chamber 47 and diaphragm 52, control the flow of water into the distiller. The expansion of fluid within the chamber 47 deflects the diaphragm 52 which acts through a plunger 54 to open a check valve 56. The Kirschman et al patent thus requires a relatively complex thermocoupling means between the outlet water pipe 19 and the thermostat 17. The Kirschman et al patent briefly mentions at column 2, lines 24-27 that the temperature of the preheated water could also be sensed if desired; however, in column 2, lines 18-22, placement of the expansion chamber on the output pipe 19 is described as "the best way" for controlling the valve. Kirschman et al subsequently states, in column 6, lines 7-10, that the most precise control is obtained on the output tube 19. This teaches away from sensing the preheated water Other means for controlling a valve are also disclosed in the prior art. For example, Sech U.S. Pat. No. 4,139,418 discloses a valve 17 controlled by a liquid level control 23. The flow of water is also controlled by fluid level within distillers in U.S. Pat. Nos. 1,076,410; 3,838,016; and 4,331,514 each showing valves controlled by floats. Hand operated valves are disclosed in U.S. Pat. Nos. 771,832; 3,029,068; and 4,239,601; while U.S. Pat. No. 3,907,683 discloses regulating flow by liquid head pressure.

A distillation apparatus is also disclosed in U.S. Pat. No. 3,660,246.

The known water distillers are frequently difficult to clean which is very disadvantageous because the action of the distiller is to remove calcium, minerals and other substances from the water which causes a quick and heavy build up of materials interior of the device which can decrease the efficiency of the distiller or prevent its functioning altogether. Further, the known distillers generally do not provide means for venting dissolved gases which escape from the heated water.

SUMMARY OF THE INVENTION

An object of the present invention is to provide an efficient water distillation apparatus wherein flow of water is controlled as a function of the condenser temperature.

A further object of the present invention is to provide an easy to clean distillation apparatus which preheats the liquid to be distilled and vents dissolved gases which are released from the preheated liquid.

The present invention provides a distiller having an inlet flow path and an outlet flow path arranged in a heat exchanging manner so that inlet liquid is preheated to nearly its boiling point before reaching the evaporator portion of the apparatus. The relatively cool inlet liquid is used to cool and condense the steam from the evaporator, and, in the process, recapturing the energy from the steam for high efficiency. A thermostatically controlled inlet valve regulates the inflow of water to the apparatus as a function of the condenser temperature to minimize the amount of heated water which is disposed of as waste. Provisions are made for the escape of gases that are released from the inlet water as it preheated. The gases are released to the atmosphere before the water is boiled, thereby preventing them from being redissolved in the steam as it condenses.

A water distiller constructed in accordance with the principles of the present invention is easily cleaned, particularly all portions where impure water is in contact with the apparatus. A clean water distiller apparatus enables the heat transfer between the parts to be kept at a high level which will enhance the efficiency of the system and allow it to operate with a minimum of energy input.

BRIEF DESCRIPTION OF THE DRAWINGS

FIG. 1 is a side elevational view of a water distiller embodying the principles of the present invention.

FIG. 2 is a cross-section of the water distiller taken generally along the lines II—II of FIG. 1.

FIG. 3 is an enlarged partial cross-section of the evaporator portion of the present device taken along lines III—III of FIG. 2 and showing the lid clamping arrangement and pressure relief apparatus.

FIG. 4 is a partial cross-section of the distiller apparatus shown in FIG. 1 detailing the flow path of liquid through the apparatus.

FIG. 5 is a cross-section of an alternate embodiment of the automatic valve.

FIG. 6 is a side elevational view of a second embodiment of a water distiller constructed according to the principles of the present invention.

FIG. 7 is an enlarged side elevational view of the apparatus of FIG. 6 shown partially in cross-section.

FIG. 8 is an enlarged partial cross-section of the thermostatically controlled valve of FIG. 7.

FIG. 9 is a plan view of the apparatus of FIG. 6.

FIG. 10 is an enlarged partial cross-section of a thermostatically controlled valve taken generally along the lines X—X of FIG. 9.

FIG. 11 is a side elevational view of a third embodiment of a condensor for use with the apparatus of the present invention.

FIG. 12 is a cross-section of a further embodiment of a water distiller embodying the principles of the present invention.

FIG. 13 is a cross-section of another thermostatically controlled valve for use in the present device.

DESCRIPTION OF THE PREFERRED EMBODIMENTS

In FIG. 1 there is shown a water distiller apparatus generally at 10 which is comprised of a condensation portion 12, an evaporation portion 14, and a gas escape chimney portion 16 A water inlet control valve 18 having a body portion 19 is provided with a supply of water containing gaseous and other dissolved impurities through a conduit 20.

A first embodiment of the valve 18 is shown in greater detail in FIGS. 2 and 4 where it is seen that the conduit 20 is connected to an orifice 22 in the valve body 19 by means of a coupling 24. The valve body 19 is generally cylindrical and has an internal bore 26 which has a threaded circumference 28 at an open top end 30 and, at an opposite end, a tapered portion 32 leading to a smaller diameter bore 34 which extends through the remaining portion of the valve body 19 at a bottom end 36. The smaller diameter bore 34 is slightly flared at 38 where it exits the bottom end 36 of the valve body 19.

Carried within the bore 26 is a valve needle 40 which has a frusto-conical lower end wall 46 shaped complementary to the tapered end wall portion 32 so that it can be sealably engaged therewith to prevent the flow of liquid therebetween. The valve needle 40 is biased downwardly by a biasing means 50, such as a coil spring.

A central aperture 72 extends through the length of the valve needle 40 and carried within the central aperture 72 is a cylindrical rod-like valve stem 76 having a lower end 78 protruding beyond the frusto-conical end wall 34 of the valve needle 40. The valve stem 76 is adjusted by adjusting screw 82.

Secured against the bottom wall 36 of the valve body 19 by means of retaining members 84, such as screws, is a thermally conductive compound or material 86. The compound 86 encapsulates a thermal actuator 88, such as one commercially sold by Robertshaw of Knoxville, Tenn., having a protruding piston member 90 which extends beyond the block of conductive material 86 into the flared portion 38 of the valve body 19 and abuts against the lower end 78 of the valve stem 76.

The assembly of the valve body 19 and the thermally conductive material 86 is attached to a tubular wall 92 forming an outer wall of the condensation portion 12 of the water distiller 10. The conductive compound 86 is secured against the tubular wall 92 by an appropriate bracket 94 or other restraining means (FIG. 1) and the block is shaped to conform to the outer circumference of the tubular wall 92 such that a solid mechanical contact is made and thermal energy is readily transferred between the tubular wall 92 and the conductive material 86.

The thermal actuator 88 operates to cause the piston 90 to move upwardly with respect to FIG. 4 upon the application of thermal energy to the actuator. Thus, when thermal energy is transferred to the actuator 88, the piston member 90 moves upwardly against the valve stem 76 causing the valve needle 40 to move upwardly against the bias of the spring 50 and lift the bottom wall 46 away from the tapered bottom wall 32 of the bore 26.

An alternative embodiment of the valve means is shown in FIG. 5 at 18a. The valve means 18a has a valve body 19a which is provided with a supply of water through a conduit 20a. The conduit 20a is connected to an orifice 22a in the valve body 19a which is generally cylindrical and has an internal bore 26a, at one end of which is a tapered portion 32a leading to a smaller diameter bore 34a that extends through the remaining portion of the valve body 19a. Carried within the bore 26a is a valve ball 40a operable to sealably engage the tapered wall portion 32a to prevent a flow of liquid therebetween. The valve ball 40a a is continuously biased downwardly within the valve body 19a by a biasing means 50a such as a coil spring. A retaining means 56a, such as a retaining plug, engages a top end 62a of the spring 50a.

Secured to a bottom wall 36a of the valve body 19a by means of a threaded interconnection at 84a, is a thermally conductive compound or material 86a. The compound 86a encapsulates a thermal actuator 88a, described above, having a protruding piston member 90a which extends beyond the conductive material 86a into the valve body 19a and abuts against the valve ball 40a.

The assembly of the valve body 19a and the thermally conductive material 86a is attached to the tubular wall 92 substantially as described above. The thermal actuator 88a operates to cause the piston 90a to move upwardly with respect to FIG. 5 upon the application of thermal energy to the actuator. The upward movement of the piston member 90a causes the valve ball 40a to move upwardly against the bias of the spring 50a, thereby lifting the valve ball 40a away from the tapered bottom wall 32a of the valve body bore 26a.

With either valve embodiment 18 or 18a, the water inlet bore 22 communicates through the valve body 19 (19a) to a water conduit 96 (96a) when the valve needle 40 (valve ball 40a) is in a raised position. The conduit 96 (96a) is attached at an opposite end 100 by a coupling 102 to the condensation section 12 of the present water distiller 10.

The condensation portion 12 is comprised of the outer tubular wall 92 and an inner concentrically mounted tube 106 such that an annular space 108 is formed between the two tubes 92, 106. A plurality of inner tubes 106 may also be used to increase the surface area within the heat transfer zone of annular space 108 to provide for greater flow rates of water through the distiller. A single tube mounting arrangement is shown in FIG. 4 where it is seen that the outer tube 92 and the inner tube 106 are held in spaced relation by the annular spacing element 104. The three parts may be assembled and secured in place by appropriate means such as welding.

The annular spacer 104 has a top wall 110 which forms a bottom wall of the annular space 108 between the two tubes 92 and 106. The annular spacer 104 has a central bore 112 therethrough of a diameter substantially the same as the outer diameter of the inner tube 106 and has a portion thereof at 114 which is threaded at an open bottom end to receive a screw cap member 116. The screw cap member 116 has an end wall 118 opposite a head portion 120 which forms a bottom wall of a cylindrical space 122 interior of the inner tube 106. A seal member 124 is provided between the screw cap member 116 and the annular spacer 104 to provide a water tight seal between the members.

The annular spacer 104 has an inlet bore 125 through a portion thereof above the threaded portion 114 into which the coupling 102 is secured. In this manner, the water conduit 96 communicates with an interior space 122 within the inner tube 106. Thus, inlet water which has passed through the valve means 18 enters the inner tube 106 by means of conduit 96.

The outer tube 92 and inner tube 106 are similarly secured at a top end by means of a second annular spacer 126 which has a bottom wall 128 forming a top wall of the annular space 108 between the two tubes 92 and 106. The second annular spacer 126 similarly has an inner bore 130 of a diameter substantially equal to the outer diameter of inner tube 106 and has a threaded portion 132 near an open top end thereof to threadingly receive a top screw cap member 134. The top screw cap member 134 has a bottom face 136 opposite the head portion 138 which forms a top wall of the space 122 interior of the inner tube 106. A sealing member 140 is positioned between the top screw member 134 and the second annular spacer 126 to provide a water tight seal therebetween. Alternatively, the threaded portion 132 may be omitted and the top cap 134 could be retained in the inner bore 130 by frictional engagement and sealed by sealing means 140, such as an "O" ring. There is no appreciable pressure build-up within the inner bore 130 so a threaded connection is not absolutely required.

The top annular spacer 126 has an opening 142 therethrough below the threaded portion 132 which receives a coupling member 144 connected to a conduit 146 such that conduit 146 communicates with the interior space 122 within the inner tube 106. A second end 148 of the conduit 146 is connected by means of a coupling 150 to a bowl member 152 having an open top which forms a top end of the chimney portion 16 of the distiller 10. Water communication is thereby provided between the conduit 146 and an interior space 154 of the bowl member 152.

The chimney portion 16 of the water distiller 10 is comprised of an outer tube 156 and an inner tube 158 which is mounted concentrically within the outer tube 156 to provide an annular space 160 between the two tubes 156 and 158. The tubes 156 and 158 are also secured to the bowl member 152 by means of a screw member 162 which is received through a central opening 164 in a bottom wall 166 of the bowl member 152 which engages a nut member 168 positioned below the bottom wall 166 of the bowl member 152. The screw member 162 has a central bore 170 therethrough which has a diameter substantially the same as the outer diameter of the inner tube 158. The nut member 168 has an outer circumference substantially the same as the interior circumference of the outer tube 156 such that the outer tube can slide over and be received by the nut 168. A sealing means 171 is provided between the nut 168 and the screw 162 just below the bottom wall 166 of the bowl member 152 to prevent any water leakage between the parts. The entire assembly may be secured by appropriate means such as welding. The chimney portion 16 containing the inner tube 158 and the outer tube 156 extends downwardly to the evaporator portion 14.

The evaporator portion 14 is comprised of a tank member 172 having side walls 174 and a bottom 176 and an open top 177. A lid member 178 is provided which can be sealingly retained against the open top 177 to provide an essentially closed container. A clamping means 180, shown in FIG. 3, is used to clamp the lid portion 178 to the tank 172. Specifically, the tank side walls 174 have a curved upper lip portion 182 which curves outwardly to form a rim. The lid member 178 has an annular depression or channel 184 around the periphery thereof and has an outer circumference forming a flange 186 which extends over the rim portion 182 of the tank 172. A sealing means 188, such as an O-ring, is provided between the flange 186 and the rim 182.

The clamp 180 is comprised of a resilient band 190 having a first free end 192 which is positioned within the annular channel 184 in the lid 178 and a second end 194 pivotally captured on a lever member 196 which has a fulcrum end 198 captured under the rim lip 182 of the side wall 174. A second free end 200 of the lever member 196 can be moved toward or away from the side wall 174 of the tank 172 to selectively engage or disengage the clamping member 180. As the free end 200 is moved toward the side wall 174, the clamp engages and holds the lid member 178 securely against the side wall 174. Conversely, when the free end 200 is moved away from the side wall 174, the clamp 180 is disengaged and the lid 178 may be removed from the side wall 174. As seen in FIG. 2, a plurality of such clamps 180 are to be used in securing the lid 178 to the side walls 174 of the tank 172.

Referring back to FIG. 4, it is seen that the outer tube 156 is secured to the lid member 178 by means of a central opening 202 in the lid member 178 which is sized to receive the outer tube 156. The junction between the two parts can be secured by appropriate means, such as welding. A bottom end 204 of the outer tube 156 is approximately flush with an inner face 205 of the lid member 178. However, the inner tube 158 extends downwardly into an interior area 206 within the tank 172 to a point which may be near the bottom 176 of the tank 172.

A heating means 208, such as an electrical heating element, is provided within the tank 172 when the lid portion 178 is mounted on the top opening of the tank 172. The heating means 208 is secured to the lid 178 by appropriate fastening means 210 such that the heating means 208 is removable from the lid member 178. Appropriate electrical connections are made to the heating element 208 as shown by electrical line 212. Other heating means may alternately be employed as is well known.

An outlet opening 214 is provided through the side wall 174 of the tank 172. A conduit 216 is connected by means of a coupling 218 to the outlet 214 at a first end 220, and a second end 222 is connected to an overflow pipe 224 which has a sealed bottom end 226 and an open top end 228 (FIG. 3). The overflow pipe 224 has an outlet 230 at a level below the open top of the tank 172 such that a water level line 232 is maintained within the tank 172.

The annular space 108 between the outer tube 92 and inner tube 106 of the condensation portion 12, and the annular space 160 between the outer tube 156 and inner tube 158 of the chimney portion 16 are connected by means of a transfer tube 234. The transfer tube 234 extends between the two outer tubes 92 and 156 and connects an opening 236 in the tube 92 with an opening 238 in the tube 156 to provide communication between the two annular spaces 108 and 160.

Annular space 108 in the condensation portion 12 has an outlet 240 for distilled water through outer tube 92 just above top wall 110 of the annular spacer 104 and a water conduit 242 is connected to the outlet by appropriate coupling means 244.

Operation of the water distiller 10 is initiated with the tank 172 of the evaporator portion 14 empty and with no water anywhere within the water distiller. The inlet conduit 20 is connected to a supply of water such as a domestic water supply but which may contain dissolved gases such as ammonia, sulfur dioxide or other distasteful and obnoxious gaseous compounds, as well as dissolved minerals. At normal room temperatures, the thermal actuator 88 will cause the piston member 90 to be in a retracted position, enabling the biasing spring 50 within the valve body 19 to cause the valve needle 40 to be seated firmly against the tapered bottom wall 32 within the bore 26.

To initially fill the system with water, the user must rotate nut 68 downwardly against the top wall 30 of the valve body 19 to manually raise the valve needle 40 away from the tapered wall 32. As this occurs, water flows from conduit 20 through the valve body 19 and through conduit 96 into the interior 122 of the inner tube 106 of the condensation portion 12. As water fills the tube 106, it passes through outlet opening 142 and through conduit 146 into the bowl member 152 at the top of the chimney portion 16. The water collects in the bottom of the bowl 152 until it reaches a level 246 equal to the top of the head portion of the screw member 162, at which time it overflows through the central opening 170 and down through the interior of the inner tube 158 where it is discharged into the interior space 206 within the tank 172.

As the water level within the tank 172 rises, the heating means 208 may be energized to begin heating the water within the tank 172. Once the water level has reached the maximum water level 232, which has been predetermined, excess water flows out through outlet 214 and through overflow tube 224 to drain through conduit 232. At this point, the nut 68 may be rotated away from the top wall 30 of the valve body 19 and the inflow of water may be reduced or stopped.

Alternatively, the system may be filled with water manually by pouring water into the evaporator tank 172 either prior to fastening the lid 178 or by pouring the water into the bowl 152 where it will flow down inner tube 158 to the evaporator tank 172.

As the water within the tank 172 heats up to its boiling point, the water will boil into steam and the steam will rise through the annular space 160 between the outer tube 156 and inner tube 158 of the chimney portion 16 and will pass through the transfer tube 234 to the annular space 108 between the outer tube 92 and inner tube 106 in the condensation portion 12. Since the inner tube 106 will be filled with water well below boiling temperature, the steam in the annular space 108 will cool and condense and will collect near the bottom of the annular space 108 where it will exit through discharge opening 240 to conduit 242. Each of the tubes 92, 106, 156 and 158 should be constructed of a thermally conductive material such as stainless steel to assist in heat transfer between the fluids in the tubes.

As this process continues, the outer tube 92 will begin to heat up through its contact with the steam and the hot condensed water and this heat will be transferred to the thermal actuator 88 by means of the heat transfer block 86. This increase in heat will cause the thermal actuator 88 to move the piston 90 upwardly against the valve stem 76 which will in turn cause the valve needle 40 to move away from the tapered wall 32. The degree of movemen of the piston 90 is directly related to the temperature of the tube 92 at the point of attachment with the block 86, so as the temperature of tube 92 increases, the thermal actuator 88 will cause the inlet flow of water to increase, thereby providing a continuous additional supply of relatively cold water within the inner tube 106 to cool and condense the steam in the annular space 108. The adjusting screw 82 can be used to provide the proper adjustment for the valve stem 76. Alternatively, the valve stem 76 can have a threaded top end so that its position within the valve needle 40 can be threadingly adjusted. The operation of the alternative embodiment of the valve means 18a shown in FIG. 5 operates in substantially the same manner as described above The height of the condensation portion 12 below the transfer tube 234 is to be selected in accordance with the diameters and the surface areas of the two tubes 92 and 106 to provide the necessary cooling surface on tube 106 which will assure an appropriate outflow of distilled water through conduit 242. In a prototype model, a height of approximately 56 cm (22 inches) was used in the condensation portion 12 with the outer tube 92 having a diameter of 3.8 cm (1.5 inches) and the inner tube 106 having a diameter of 2.5 cm (1 inch). This resulted in a flow of distilled water of approximately 1.9 liter/hr. (0.5 gal./hr.). Increasing the surface area of the tubes would result in a greater flow of water. As described above, this can be done by using a plurality of tubes 106 within tube 92.

As the inlet water moves upwardly through the interior of inner tube 106 it increases in temperature due to the absorption of heat energy from the steam and it has been observed in prototype water distillers embodying the principles of the present invention that the temperature of water collecting in the bowl member 152 is approximately 820° C. (180° F.) At this temperature, much of the dissolved gases in the water will be released to the atmosphere through the open top of the bowl 152. As this hot water flows downwardly through the interior of the inner tube 158 toward the tank 172, it continues to heat up until it reaches a temperature just below boiling temperature at the bottom of the inner tube 158 where it is discharged into the tank 172. Thus, virtually all of the remaining dissolved gases will be released from the water as it passes down through the inner tube 158 and the gases will rise within the tube 158 to vent into atmosphere through the top opening of the bowl 152. The preheated water entering the tank 172 is heated further by the heating element 208 until it boils and turns into steam as described above.

To provide an exit for any remaining dissolved gases, it has been found useful to provide a small vent opening 248 near the top end of annular space 108 to form a pressure relief. However, there is not any substantial pressure build-up within the evaporator portion 14 of the water distiller since there is continuous open communication through outlet 214 to the overflow pipe 224.

Thus, it is seen that there is provided an embodiment of a water distiller apparatus in which inflowing water is preheated by condensing steam such that entrapped and dissolved gases are dissipated and removed from the water before it arrives at an evaporator chamber, and the inflow of water is automatically controlled by a valve means which is responsive to temperature. As the temperature in the condensation portion increases, the valve will automatically open to increase the flow of water through the system which will thereby cause the temperature in the condensation portion to decrease until an equalibrium is achieved which will maximize the heat utilized and will minimize the amount of water being discharged through the overflow tube 224. In this manner, manual adjustment is only required to initially fill the system with water and once the water in the tank 172 is boiling, the manual adjustment is removed and the water distiller will operate automatically.

The entire system can be disassembled for easy cleaning, that is, the lid 178 may be removed from the tank 174 such that the tank may be completely removed to allow the interior of the tank to be cleaned. At the same time, the heating element would be exposed thereby providing complete access for cleaning. The tubes are linear and are provided with removable end caps so that they cleaned easily. All conduits 96, 146 and 242 are attached by removable fittings and so may be removed for cleaning or replacement. The valves 18 and 18a may also be easily disassembled for cleaning. Thus, the efficiency of the apparatus may be maintained without the need for specialized cleaning equipment.

A second embodiment of the present invention is shown in FIG. 6 and includes a water heating tank 172, a gas escape chimney 16, a transfer tube 234, a conduit 146, and a condensation portion 12a. The condensation portion 12a of the second embodiment includes an air blower 300 connected to direct a flow of forced air into the condensation portion 12a. The condensation portion 12a of FIG. 6 is of a larger diameter than that of the first embodiment and includes a plurality of cooling tubes 338 therein as can be seen in FIG. 7. The second embodiment includes many other features of the previously described embodiment and further includes a thermostatically controlled valve 302 connected to the inlet conduit 20 and mounted within the tube 106a where it controls the inflow rate of water into the distiller 10. The thermostatically controlled valve 302 includes a thermostat 304 mounted within the inlet tube 106 spaced from the valve 302.

The thermoresponsive valve 302 is shown in more detail in FIG. 8 and includes a water inlet opening 306 through which water from the inlet conduit 20 enters. A valve needle 308 is biased by biasing means 310, such as a spring, against a frusto-conical end wall 312. The valve needle 308 includes an extended portion 314 that extends through a bore 316 at the center of the frusto-conical end wall 312. Abutting the extended portion 314 is a rod member 318 which is slidably disposed within a tubular member 320. The tubular member 320 is threadably received in the valve body 322 at a first end thereof and has threadably mounted therein a connection member 324 of the thermostat 304. The connection member 324 has concentrically mounted therein an actuating pin 326 which moves in response to the operation of the thermostat 304. Openings 328 are formed in the tubular member 320 at a position along its length to form water outlets. The valve body 322 is threadably received into a receiving portion 330 of the tube 106. The valve body 322 includes means in a lower end thereof by which it can be threadingly inserted such as the slot 332. The receiving portion 330 of the tube 106 includes an annular channel 334 for alignment with the water inlet bore 306. A sealing means 336, such as an O-ring, may be included between the receiving portion 330 and the valve body 322.

The valve 302 of the second embodiment operates as follows: as steam and condensate move through the condensation portion 12a of the water distiller 10, heat is tranferred to the inflowing liquid in the tube 106a. As the temperature of the liquid within the tube 106a increases to a predetermined value, the thermostat 304 mounted within the tube 106a is attached. Operation of the thermostat 304 causes the actuating pin 326 to move downwardly with respect to FIG. 8, pushing pin 320 against the extended portion 314 of the valve needle 308. As force is exerted by the actuating pin 326, the valve needle bias at 310 is overcome and incoming fluid is allowed to flow from the intake opening 306, between the valve needle 308 and the end wall 312, through the interior of the tube 320 and out through the openings 328. When a sufficient quantity of relatively cool inflowing liquid has flowed through the valve 302, the temperature of the liquid adjacent the thermostat 304 is lowered, causing the thermostat actuating pin 326 to move upwardly with respect to FIG. 8. This enables the bias spring 310 to force the valve needle 308 against the end wall 312, closing the valve. Thus, it can be seen that the present thermostatically controlled valve 302 operates as a function of the temperature of the preheated water within the inlet tube 106a, and further that the thermostatically controlled valve 302 senses the temperature of the liquid directly by means of a thermostat located within the water flow. The direct sensing of the water temperature overcomes many of the problems associated with attaining a good thermal connection between the valve 302 and the medium being sensed. Direct sensing of the pertinent medium decreases the response time of the valve 302, thereby increasing the energy efficiency of the distiller device 10. The valve 302 of the second embodiment can also be used in the distiller 10 of the first embodiment.

In the second embodiment shown in FIGS. 6 through 10, not only is the incoming liquid used as a cooling medium in the condenser portion 12a but air is also used as a cooling medium. A plurality of air conduits 338 are provided within the condensation portion 12a through which air is forced. The air conduits 338 are in communication with an air intake chamber 340 which is fed by the air blower 300. Top portions 342 of the air conduits 338 are open to exhaust the warmed air to the atmosphere and inter-conduit spaces 344 are closed at the top of the condenser 12a that steam produced by the evaporating portion 14 is held within the spaces 344 where it is cooled by air flow through the air conduits 338 and by the inlet water in the tube 106a.

Operation of the second embodiment is similar to that of the first embodiment with the exception of the air blower 300, which blows air into the air intake space 340 and then upward through the air conduits 338 and out of the open top 342. The air flow through the air conduits 338 carries away heat from the condensing steam within the condenser portion 12a at a greater rate so that the output volume of the distiller device 10 may be increased.

As can be seen in FIG. 9, the air conduits 338 are arranged in a symmetrical pattern within the distiller portion 12a so that a large surface area is presented for heat transfer while enabling a high volume of air to flow through the air conduits 338. As also can be seen in FIG. 9, the water input conduit 20 is mounted at a coupling 24 spaced from the thermoresponsive valve 302. The input conduit 20 and coupling 24 are connected to the valve 302 by an extended input tube 350 as shown in FIG. 10.

FIG. 11 shows a third embodiment where cooling is accomplished by an external water supply in which a plurality of fluid carrying interior tubes 352 are arranged within a condensing portion 12b. Relatively cool water, or other fluid, is fed through a condenser water input 354 into a preliminary chamber 356. Afterwards the condenser cooling fluid flows upwardly through the interior tubes 352 into an upper chamber 358 and out of a condenser output 360. In the third embodiment, the condenser portion 12b includes a cap 362 to prevent escape of the cooling fluid and may optionally include a sealing means 364, such as an O-ring.

The third embodiment provides rapid cooling of the condensation portion 12b and, consequently, provides a high volume output of distilled water.

FIG. 12 shows another embodiment of the present invention having many of the features discussed in conjunction with earlier figures, including the concentrically mounted inner tube 106 within the condensation portion 12, as in FIGS. 1 through 4, as well as the thermostatically controlled valve 302 mounted within the tube 106, as in FIGS. 7 and 8. The FIG. 12 embodiment includes the advantages of the valve 302 and the thermostat 304 mounted within the tube 106 in an embodiment with a single tube 106 within the condenser 12 and thus requires no external cooling source. Energy efficiency is thus maximized in the embodiment of FIG. 12 wherein a greater portion of the heat energy used to boil the water in the distillation process is recaptured in the condenser portion 12 and applied to preheat incoming water. The use of an external cooling source, such as an air blower or separate water supply, is eliminated.

The evaporator portion 14 includes the tank member 172 in which water is heated. The tank 172 is detachably mounted to the lid portion 178 by a clamp 370 which operates by toggle action to secure the bowl 172 to the annular rim 184 of the lid 178. The clamp 370 includes a bail wire 372 extending under the bowl 172. The bail wire 372 is U-shaped and extends upward on either side of the bowl 172. Ends 374 of the bail 372 are pivotally attached to a toggle member 376. The toggle member 376 includes laterally extending portions 378 which span the diameter of the lid 178, at each end of which the ends 374 of the bail wire 372 are attached, and a semicircular portion 380 which embraces the chimney 16. The toggle member 376 is hingedly connected to the chimney 16 so that it pivots between a closed position shown in solid outline, and an open position, shown in dotted outline. In the closed position, the semicircular portion 380 of the toggle member 376 embraces the chimney 16 and the bail wire 372 is drawn upward to hold the bowl member 172 against the lid 178.

When the toggle member 376 is pulled away from the chimney 16, toggle action causes the toggle member 376 to snap to its open position, as shown, and the bail wire 372 is thereby moved downward sufficiently so that it may be pivoted from under the bowl 172. The bowl 172 may thereafter be easily removed from the device 10 for cleaning.

Once clean, the bowl 172 is placed in position and the bail 372 is pivoted thereunder, after which the toggle member 376 is snapped into its closed position so that the bail 372 holds the bowl 172 tightly against the lid 178. Thus, the bowl 172 may be removed and replaced easily with only the operation of a single fastening member.

Operation of the device shown in FIG. 12 to produce distilled water is otherwise substantially identical to the above described and shown devices.

FIG. 13 shows an alternate embodiment of a thermostatically controlled valve for use in the device of the present invention. The valve 386 is for use with the thermostat 304 shown in FIGS. 7 and 8 and includes the connection member 324 in which the actuating pin 326 is mounted. The valve of FIG. 13 includes a valve pin 388 which is biased by a spring 390 which engages a threadably connected washer 392 at the top of the valve pin 388 and engages an annular ledge 394 within a valve body 396. At spaced locations on the valve pin 388 a pair of O-rings 398 and 400 are mounted. An opening 402 extends from the water inlet conduit 20 and communicates with an interior opening 404 within the valve body 396 in which the valve pin 388 is disposed. A pressure relief opening 406 extends from the interior opening 404 below the valve pin 388 to the interior space 122 within the tube 106.

The spring 390 biases the valve pin 388 upwardly against the actuating pin 326. When the thermostat 304 is in the closed position, the O-rings 398 and 400 straddle the intake opening 402 so that water is prevented from flowing into the space 404.

When the water within the tube 106 reaches a predetermined temperature, the thermostat 304 operates forcing the actuating rod 326 downwardly against the valve pin 388 in opposition to the biasing effect of the spring 390 so that the O-ring 400 is moved below the intake opening 402. Water thus is allowed to flow through the intake conduit 20, through the intake opening 402, and into the space 404 where it passes upward into the connecting member 324 and out the opening 328. As cool water flows into the tube 106, the temperature falls until the thermostat 304 operates to enable the actuating pen 326 to be driven upwardly by the biasing spring 390 so that the O-ring 400 again is above the intake opening 402, thus cutting off the inflow of water into the tube 106.

The lower O-ring 398 is provided to form a seal between the valve pin 388 and the valve body 396 below the intake opening 402. The O-ring 398 prevents water from flowing through the pressure relief opening 406 from the intake opening 402. Movement of the valve pin 388 would be hindered by pressure differences generated below the lower O-ring 398, and thus the pressure relief opening is provided through which water flows during movement of the valve pin 388. Numerous sealing means, such as O-rings, are shown in FIG. 13 to provide water tight operation of the device.

Each of the embodiments disclosed include linear tubes and easily accessible parts and are disassemblable to provide easy cleaning.

Thus, there has been shown and described several embodiments of a water distilling device including a first embodiment in which the condensate is cooled by inflowing water, a second embodiment in which the condensate is cooled by inflowing water and air flow, and a third embodiment in which the condensate is cooled by a separate source of cooling liquid. Thermostatically controlled valves are also disclosed associated with the condensation portions of the water distiller 10 which valves respond to the temperature of the condensation portions during the operation of the water distilling device 10. A first embodiment of thermostatically controlled valve is thermally coupled to the outside of the condensing portion 12 while a second embodiment of the valve includes a thermostat mounted within the water intake conduit 106a so that it senses the temperature of the preheated water therein.

As is apparent from the foregoing specification the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim:

1. A distilling apparatus comprising:
    an evaporator including a heater and a removable tank within which said heater is disposed, a lid removably affixed over said tank, a substantially vertical chimney extending from said lid and connected with said tank so that vapor produced from a liquid to be distilled passes therethrough, an inlet conduit providing a fluid flow path for said liquid to be distilled to said tank of said evaporator, said inlet conduit forming an inner tube disposed extending within said chimney substantially coaxially of said chimney, a condenser connected to said evaporator, at least a portion of said inlet conduit is disposed within said condenser so that heat is transmitted through said inlet conduit to preheat incoming liquid by condensing vapors passed in said condenser, an outlet connected from said condenser through which condensed liquid is removed, a valve connected to control the flow of liquid into said inlet conduit, a thermostat in thermal communication with said condenser at an exterior surface thereof, said thermostat including means for connecting said thermostat to said valve so that said thermostat operates said valve.

2. A distilling apparatus as claimed in claim 1 further comprising a vent in said inlet conduit.

3. A distilling apparatus as claimed in claim 1 wherein said tank is secured to said lid of said evaportator by a toggle.

4. A distilling apparatus as claimed in claim 1 wherein said condenser includes a plurality of heat exchanger elements disposed therein.

5. A distilling apparatus comprising: an evaporator including a heater and a removable tank within which said heater is disposed, lid removably affixed over said tank, a substantially vertical chimney extending from said lid and connected with said tank so that vapor produced from a liquid to be distilled passes therethrough, an inlet conduit providing a fluid flow path for said liquid to be distilled to said tank of said evaporator, said inlet conduit forming an inner tube disposed extending within said chimney substantially coaxially of said chimney, a condenser connected to said evaporator, at least a portion of said inlet conduit is disposed within said condenser so that heat is transmitted through said inlet conduit to preheat incoming liquid by condensing vapors passed in said condenser, an outlet connected from said condenser through which condensed liquid is removed, a valve connected to control the flow of liquid into said inlet conduit, a thermostat in thermal communication with said condenser said thermostat including means for connecting said thermostat to said valve so that said thermostat operates said valve, said thermostat being disposed within said inlet conduit and being responsive to the temperature of said preheated liquid.

6. A distilling apparatus as claimed in claim 5 further comprising biasing means for biasing said valve to a closed position, said value including a rigid actuator connected between said thermostat and said valve for opposing said biasing means.

7. A distilling apparatus comprising: an evaporator including a liquid tank for charging with a liquid to be distilled having a removable top, said top defining an opening therethrough, means for heating the liquid within said tank, an exhaust chimney extending from said liquid tank including a first end connected with said opening, said exhaust chimney further including first and second concentrically mounted tubes wherein said first tube is a vapor outlet tube and said second tube is a tank inlet tube disposed within said first tube, venting means at a second end of said exhaust chimney providing access to the atmosphere for said tank inlet tube, a condenser connected with said exhaust chimney, said condenser including an outer tube connected with said first vapor outlet tube and at least one inner tube disposed therein, said at least one inner tube comprising a condenser inlet tube in communication with said tank inlet tube, a condensate outlet connected to said outer tube of said condenser, a liquid inlet connected to said condenser inlet tube to supply liquid to be distilled, a thermo-responsive valve mounted to control the flow of liquid in said liquid inlet, said thermo-responsive valve including a thermostat mounted substantially centrally within said condenser inlet tube and connected to operate said valve as a function of temperature of the liquid within said condenser inlet tube.

8. A distilling apparatus as claimed in claim 7 wherein said venting means includes a bowl shaped receptacle at a second end of tank inlet tube, and a first opposite end of said tank inlet tube extending into said liquid tank.

9. A distilling apparatus as claimed in claim 7 wherein said heating means includes an electrical heating element.

10. A distilling apparatus as claimed in claim 7 wherein said at least one inner tube comprises a plurality of inner tubes within said condensation portion, and means for causing a flow of cooling medium through at least some of said plurality of inner tubes.

11. A distilling apparatus as claimed in claim 10 wherein said flow causing means includes an air blower connected with first ends of said inner tubes, and second ends of said inner tubes being open to the atmosphere.

12. A distilling apparatus as claimed in claim 10 wherein said flow causing means includes means for causing water flow through said inner tubes.

* * * * *